(12) United States Patent
Kim et al.

(10) Patent No.: US 10,385,161 B2
(45) Date of Patent: Aug. 20, 2019

(54) PHOSPHONIUM-BASED COMPOUND, EPOXY RESIN COMPOSITION CONTAINING SAME, SEMICONDUCTOR DEVICE MANUFACTURED USING SAME

(71) Applicant: SAMSUNG SDI CO., LTD., Yongin-si, Gyeonggi-do (KR)

(72) Inventors: Min Gyum Kim, Suwon-si (KR); Jin Woo Choi, Suwon-si (KR); Ki Hyeok Kwon, Suwon-si (KR); Dong Hwan Lee, Suwon-si (KR); Joo Young Chung, Suwon-si (KR); Jin Min Cheon, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 166 days.

(21) Appl. No.: 15/523,501

(22) PCT Filed: Jan. 22, 2016

(86) PCT No.: PCT/KR2016/000725
§ 371 (c)(1),
(2) Date: May 1, 2017

(87) PCT Pub. No.: WO2016/167449
PCT Pub. Date: Oct. 20, 2016

(65) Prior Publication Data
US 2017/0306079 A1  Oct. 26, 2017

(30) Foreign Application Priority Data
Apr. 15, 2015  (KR) ........................ 10-2015-0053405

(51) Int. Cl.
| | |
|---|---|
| *H01L 23/28* | (2006.01) |
| *C08G 59/68* | (2006.01) |
| *C08L 63/00* | (2006.01) |
| *C07F 9/54* | (2006.01) |
| *C07C 39/10* | (2006.01) |
| *C07C 39/15* | (2006.01) |
| *C07C 49/83* | (2006.01) |
| *C07C 255/53* | (2006.01) |
| *C08K 3/36* | (2006.01) |
| *H01L 23/29* | (2006.01) |
| *H01L 23/31* | (2006.01) |
| *C07C 39/08* | (2006.01) |
| *C07C 39/17* | (2006.01) |
| *C07C 39/235* | (2006.01) |

(52) U.S. Cl.
CPC ............ *C08G 59/688* (2013.01); *C07C 39/08* (2013.01); *C07C 39/10* (2013.01); *C07C 39/15* (2013.01); *C07C 39/17* (2013.01); *C07C 39/235* (2013.01); *C07C 49/83* (2013.01); *C07C 255/53* (2013.01); *C07F 9/5442* (2013.01); *C08K 3/36* (2013.01); *H01L 23/293* (2013.01); *H01L 23/3107* (2013.01); *C07C 2603/18* (2017.05)

(58) Field of Classification Search
None
See application file for complete search history.

(56) References Cited

U.S. PATENT DOCUMENTS

| | | | | |
|---|---|---|---|---|
| 9,428,632 | B2 * | 8/2016 | Kim | ...................... C07F 9/5442 |
| 9,633,922 | B2 * | 4/2017 | Ogawa | ................. C08G 59/688 |
| 2004/0058160 | A1 * | 3/2004 | Nagata | ................. C08G 59/621 |
| | | | | 428/413 |
| 2014/0179827 | A1 * | 6/2014 | Kim | ...................... C07F 9/5442 |
| | | | | 523/400 |

FOREIGN PATENT DOCUMENTS

| | | | | |
|---|---|---|---|---|
| CN | 101107285 | A | 1/2008 | |
| JP | 2003292582 | A * | 10/2003 | ............ C08G 59/62 |
| JP | 2004-002574 | A | 1/2004 | |
| JP | 2004-269586 | A | 9/2004 | |
| JP | 2004-300431 | A | 10/2004 | |
| JP | 2006-307131 | A | 11/2006 | |
| KR | 2007-0103419 | A | 10/2007 | |
| KR | 2014-0082528 | A | 7/2014 | |

OTHER PUBLICATIONS

Machine translation of JP-2003292582-A (no date).*
Machine translation of JP-2004269586-A (no date).*
International Search Report PCT/KR2016/000725, dated May 18, 2016.
Office Action dated Feb. 22, 2017 in the corresponding Korean Patent Application No. 10-2015-0053405.
Chinese Office Action dated Nov. 27, 2018.

* cited by examiner

*Primary Examiner* — Michael J Feely
(74) *Attorney, Agent, or Firm* — Lee & Morse, P.C.

(57) ABSTRACT

The present invention relates to a phosphonium-based compound represented by chemical formula 1, an epoxy resin composition containing the same, and a semiconductor device manufactured by using the same.

10 Claims, 1 Drawing Sheet

【FIG. 1】
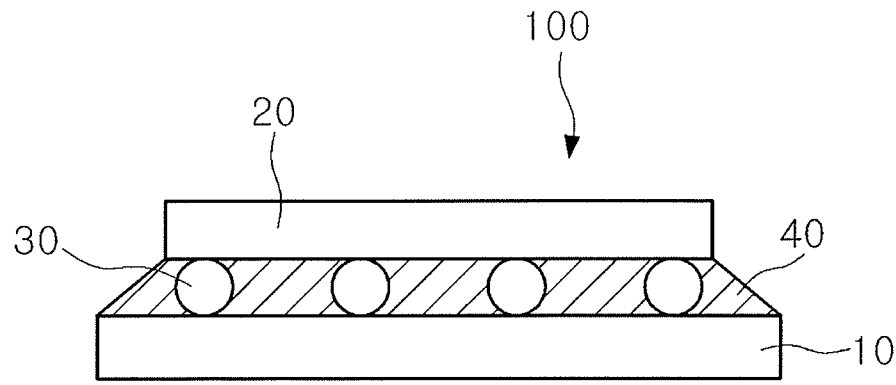
【FIG. 2】
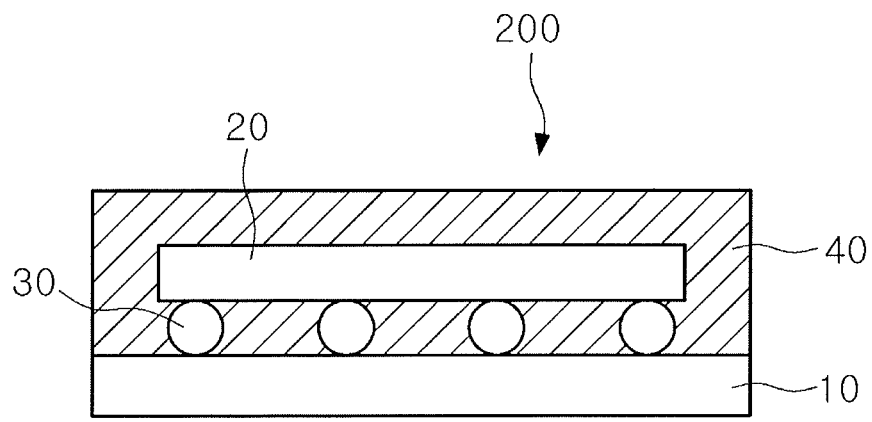
【FIG. 3】
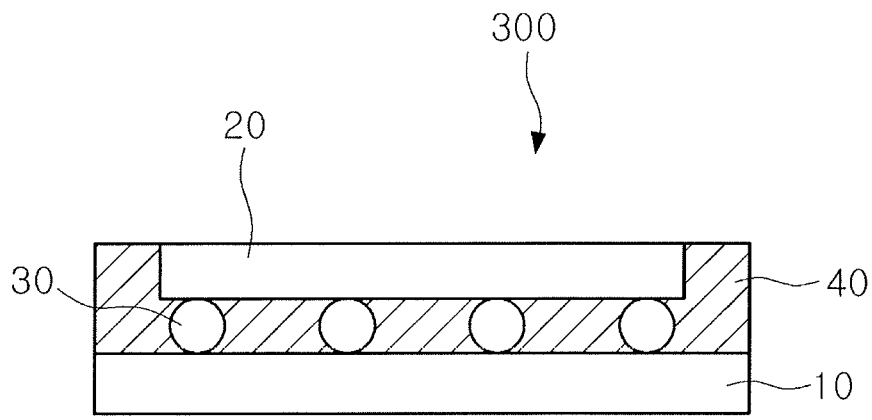

PHOSPHONIUM-BASED COMPOUND, EPOXY RESIN COMPOSITION CONTAINING SAME, SEMICONDUCTOR DEVICE MANUFACTURED USING SAME

CROSS REFERENCE TO RELATED APPLICATIONS

This is the U.S. national phase application based on PCT Application No. PCT/KR2016/000725, filed Jan. 22, 2016, which is based on Korean Patent Application No. 10-2015-0053405, filed Apr. 15, 2015, the entire contents of all of which are hereby incorporated by reference.

TECHNICAL FIELD

The present invention relates to a phosphonium compound, an epoxy resin composition including the same and a semiconductor device prepared using the same.

BACKGROUND ART

Transfer molding is widely used as a method of packaging semiconductor devices, such as ICs (integrated circuits) and LSI chips, with epoxy resin compositions to obtain semiconductor devices due to its advantages of low cost and suitability for mass production. In transfer molding, modification of epoxy resins or phenol resins as curing agents can lead to improvements in the characteristics and reliability of semiconductor devices.

Such epoxy resin compositions include an epoxy resin, a curing agent, a curing catalyst, and the like. As the curing catalyst, imidazole catalysts, amine catalysts, and phosphine catalysts have usually been utilized.

With the trend toward compact, lightweight and high-performance electronic devices, high integration of semiconductor devices has been accelerated year by year. Problems unsolved by conventional epoxy resin compositions arise with increasing demand for surface mounting of semiconductor devices. Other requirements for packaging materials for semiconductor devices are rapid curability to improve productivity and storage stability to improve handling performance during distribution and storage.

Korean Patent Publication No. 10-2014-0082528A discloses an epoxy resin curing catalyst using tetravalent phosphonium salts.

DISCLOSURE

Technical Problem

It is one aspect of the present invention to provide a compound for curing catalysts capable of accelerating curing of an epoxy resin, having good flowability upon molding and high curing strength, and being curable even at short curing periods of time.

It is another aspect of the present invention to provide a compound for curing catalysts capable of accelerating curing of an epoxy resin at a low temperature.

It is a further aspect of the present invention to provide a compound for curing catalysts having high storage stability which catalyzes curing only at a desired curing temperature but does not show any curing activity at temperatures deviating from desired curing temperatures.

It is yet further aspect of the present invention to provide a semiconductor device including the epoxy resin composition.

Technical Solution

One aspect of the present invention relates to a phosphonium compound. The phosphonium compound is represented by Formula 1:

[Formula 1]

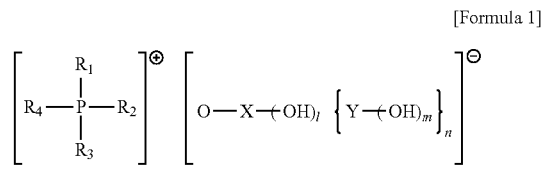

wherein $R_1$, $R_2$, $R_3$, $R_4$, X, Y, l, m and n are as defined in the detailed description of the invention.

In the phosphonium compound, $R_1$, $R_2$, $R_3$, and $R_4$ may be a $C_6$ to $C_{30}$ aryl group.

When $R_1$, $R_2$, $R_3$, and $R_4$ are a $C_6$ to $C_{30}$ aryl group, at least one of $R_1$, $R_2$, $R_3$, and $R_4$ may be substituted with a hydroxyl group.

X may be a $C_6$ to $C_{30}$ aryl group.

The phosphonium compound may be any one of compounds represented by Formulae 1a to 1f:

[Formula 1a]

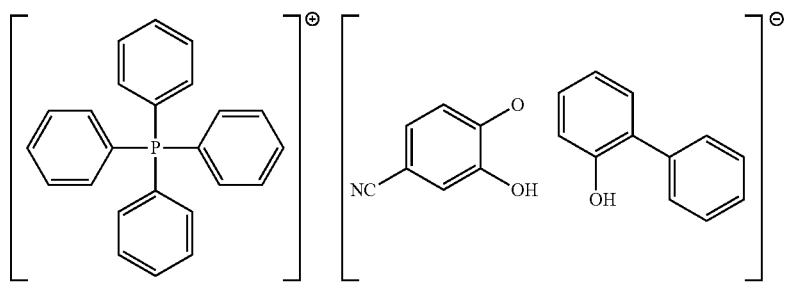

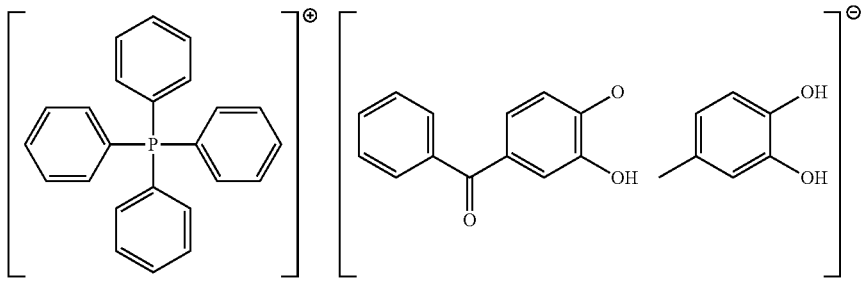 [Formula 1b]
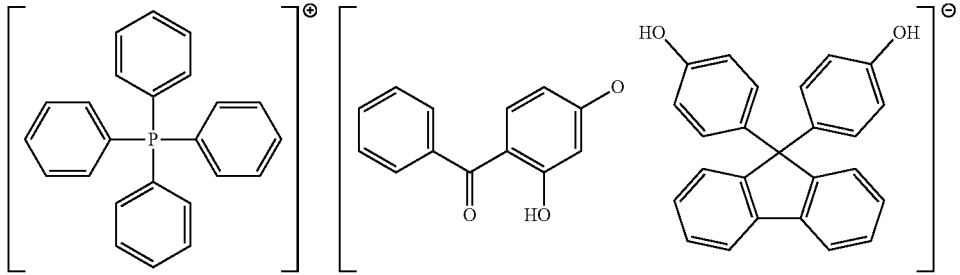 [Formula 1c]
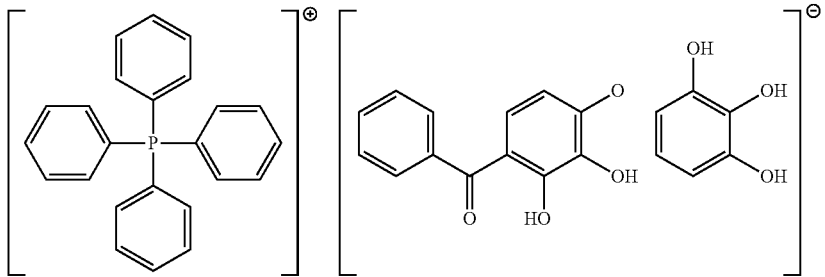 [Formula 1d]
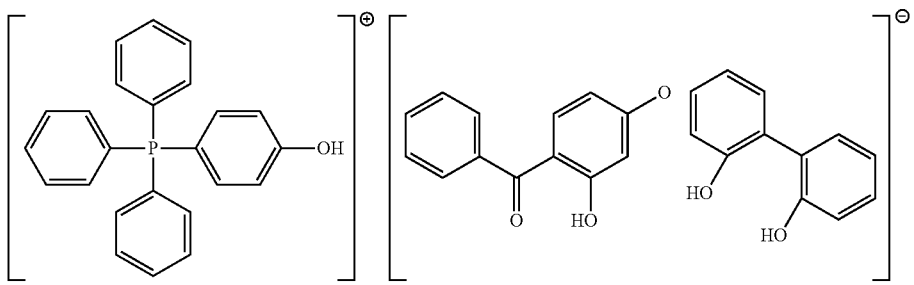 [Formula 1e]
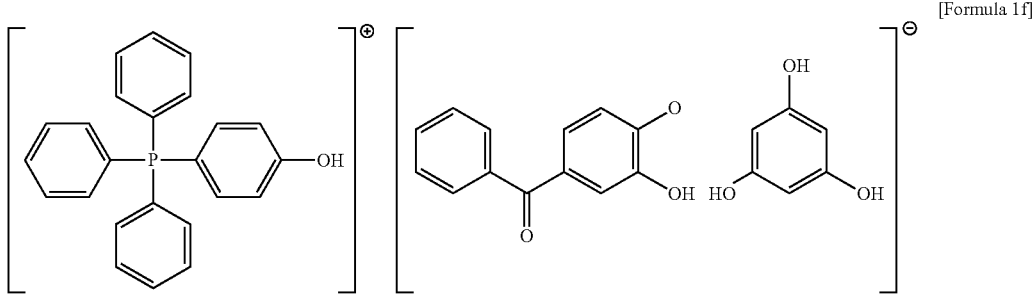 [Formula 1f]

Another aspect of the present invention relates to an epoxy resin composition. The epoxy resin composition includes an epoxy resin, a curing agent, inorganic fillers, and a curing catalyst, wherein the curing catalyst includes the phosphonium compound acting as a curing accelerator.

The epoxy resin may include at least one of bisphenol A type epoxy resins, bisphenol F type epoxy resins, phenol novolac type epoxy resins, tert-butyl catechol type epoxy resins, naphthalene type epoxy resins, glycidylamine type epoxy resins, cresol novolac type epoxy resins, biphenyl type epoxy resins, linear aliphatic epoxy resins, cycloaliphatic epoxy resins, heterocyclic epoxy resins, spiro ring-containing epoxy resins, cyclohexane dimethanol type epoxy resins, trimethylol type epoxy resins, and halogenated epoxy resins.

The curing agent may include a phenol resin.

The curing agent may include at least one of phenol aralkyl type phenol resins, phenol novolac type phenol resins, xyloc type phenol resins, cresol novolac type phenol resins, naphthol type phenol resins, terpene type phenol resins, polyfunctional phenol resins, dicyclopentadiene-based phenol resins, novolac type phenol resins synthesized from bisphenol A and resorcinol, polyhydric phenolic compounds, including tris(hydroxyphenyl)methane and dihydroxybiphenyl, acid anhydrides, including maleic anhydride and phthalic anhydride, metaphenylenediamine, diaminodiphenylmethane, and diaminodiphenylsulfone.

The curing catalyst may be present in an amount of about 0.01% by weight (wt %) to about 5 wt % in the epoxy resin composition.

The phosphonium compound may be present in an amount of about 10 wt % to about 100 wt % in the curing catalyst.

The epoxy resin composition may have a curing shrinkage rate of about 0.4% or less, as calculated according to Equation 1:

Curing shrinkage=|C−D|/C×100         <Equation 1> wherein Equation 1, C is the length of a specimen obtained by transfer molding of an epoxy resin composition at 175° C. under a load of 70 kgf/cm², and D is the length of the specimen after post-curing the specimen at 170° C. to 180° C. for 4 hours and cooling.

The epoxy resin composition may have storage stability of about 80% or more, as calculated according to Equation 2:

Storage stability=(F1−F0)/F0×100         <Equation 2> wherein F1 is the flow length (inches) of the epoxy resin composition measured after storing the epoxy resin composition at 25° C. and 50% RH (relative humidity) for 72 hours using a transfer molding press at 175° C. and 70 kgf/cm² in accordance with EMMI-1-66, and F0 is the initial flow length (inches) of the epoxy resin composition.

Another aspect of the present invention relates to a semiconductor device encapsulated with the epoxy resin composition.

Advantageous Effects

The present invention may provide a phosphonium compound capable of accelerating curing of an epoxy resin and curing of an epoxy resin at a low temperature.

Further, the epoxy resin composition including the phosphonium compound according to the present invention may minimize viscosity change even at predetermined ranges of time and temperature. As a result, the epoxy resin composition obtained after curing at high temperature does not exhibit any deterioration in moldability, mechanical, electrical, and chemical properties of molded products due to decrease in flowability.

BRIEF DESCRIPTION OF DRAWINGS

FIG. 1 is a cross sectional view of a semiconductor device according to one embodiment of the present invention.

FIG. 2 is a cross sectional view of a semiconductor device of another embodiment of the present invention.

FIG. 3 is a cross sectional view of a semiconductor device of a further embodiment of the present invention.

BEST MODE

As used herein, the term "substituted" in "substituted or unsubstituted" means that at least one hydrogen atom in the corresponding functional groups is substituted with a hydroxyl group, a halogen atom, an amino group, a nitro group, a cyano group, a $C_1$ to $C_{20}$ alkyl group, a $C_1$ to $C_{20}$ haloalkyl group, a $C_6$ to $C_{30}$ aryl group, a $C_3$ to $C_{30}$ heteroaryl group, a $C_3$ to $C_{10}$ cycloalkyl group, a $C_3$ to $C_{10}$ heterocycloalkyl group, a $C_7$ to $C_{30}$ arylalkyl group, or a $C_1$ to $C_{30}$ heteroalkyl group. The term "halo" means fluorine, chlorine, iodine or bromine.

As used herein, the term "aryl group" refers to a substituent in which all elements in the cyclic substituent have p-orbitals and the p-orbitals form a conjugated system. Aryl group may be, for example, a monocyclic or fused polycyclic $C_6$ to $C_{30}$ hydrocarbon group. Specific examples of aryl groups include phenyl groups, biphenyl groups, naphthyl groups, naphthol groups, and anthracenyl groups, without being limited thereto.

As used herein, the term "heteroaryl group" means a $C_6$ to $C_{30}$ aryl group in which a ring comprises carbon atoms and 1 to 3 heteroatoms selected from nitrogen, oxygen, sulfur and phosphorus. Examples of heteroaryl groups include, but are not limited to, pyridinyl, pyrazinyl, pyrimidyl, pyridazinyl, triazinyl, quinolinyl, isoquinolinyl, quinoxalinyl, acridinyl, quinazolinyl, cinnolinyl, phthalazinyl, thiazolyl, benzothiazolyl, isoxazolyl, benzisoxazoyl, oxazolyl, benzoxazolyl, pyrazolyl, indazolyl, imidazolyl, benzimidazolyl, purinyl, thiophenyl, benzothiophenyl, furanyl, benzofuranyl, or isobenzofuranyl.

As used herein, the term "hetero" refers to an atom selected from nitrogen (N), oxygen (O), sulfur (S) or phosphorus (P).

Phosphonium Compound

First, the phosphonium compound according to the present invention will be described.

The phosphonium compound according to the present invention is represented by Formula 1:

[Formula 1]

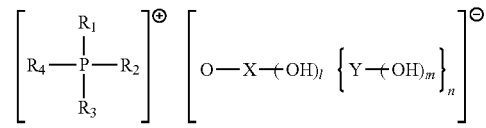

Wherein $R_1$, $R_2$, $R_3$, and $R_4$ are each independently a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a hetero atom, X and Y are different from each other and each independently a substituted or unsubstituted $C_1$ to $C_{30}$ aliphatic hydrocarbon group, a substituted or unsubstituted $C_6$ to $C_{30}$ aromatic hydrocarbon group, or a substituted or unsubstituted $C_1$ to $C_{30}$ hydrocarbon group including a hetero atom; l is an integer from 0 to 4; m is an integer from 1 to 6; and n is an integer from 1 to 5.

In Formula 1, $R_1$, $R_2$, $R_3$, and $R_4$ may be a $C_6$ to $C_{30}$ aryl group.

In Formula 1, at least one of $R_1$, $R_2$, $R_3$, and $R_4$ may be substituted with a hydroxyl group.

In Formula 1, X may be a $C_6$ to $C_{30}$ aryl group. In this embodiment, the composition including the phosphonium compound may have relatively good flowability and moldability together with good storage stability.

The phosphonium compound may be any one of compounds represented by Formulae 1a to 1f, for example:

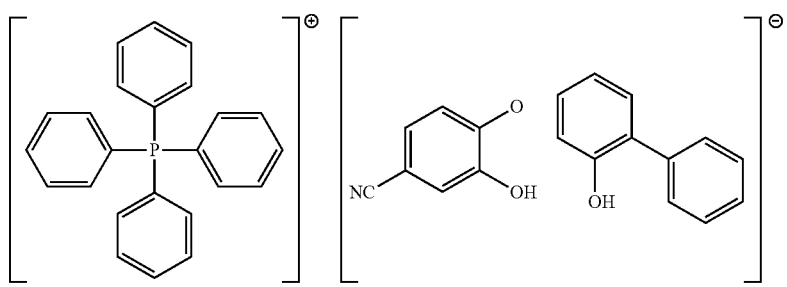

[Formula 1a]

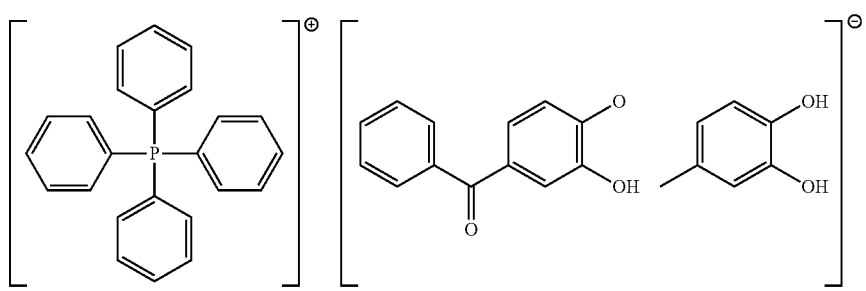

[Formula 1b]

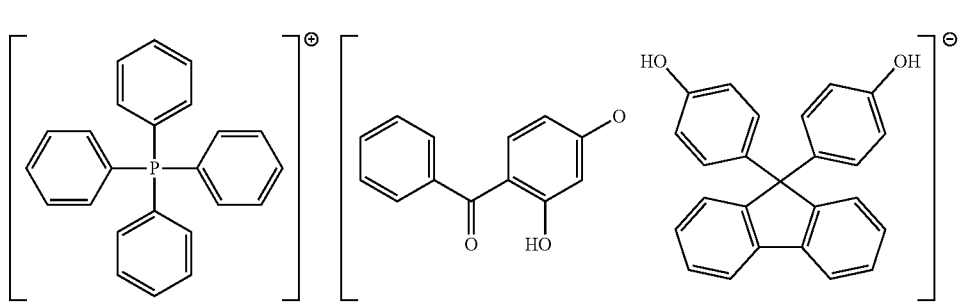

[Formula 1c]

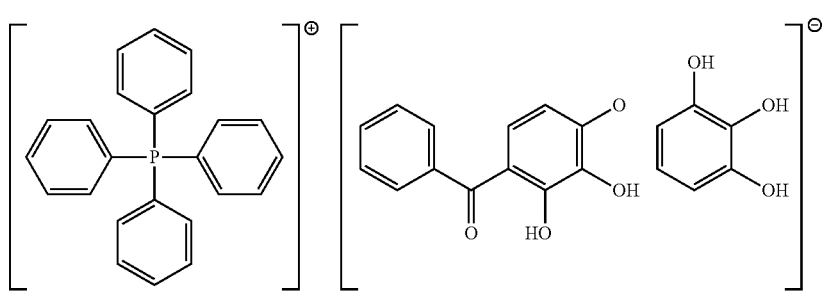

[Formula 1d]

-continued

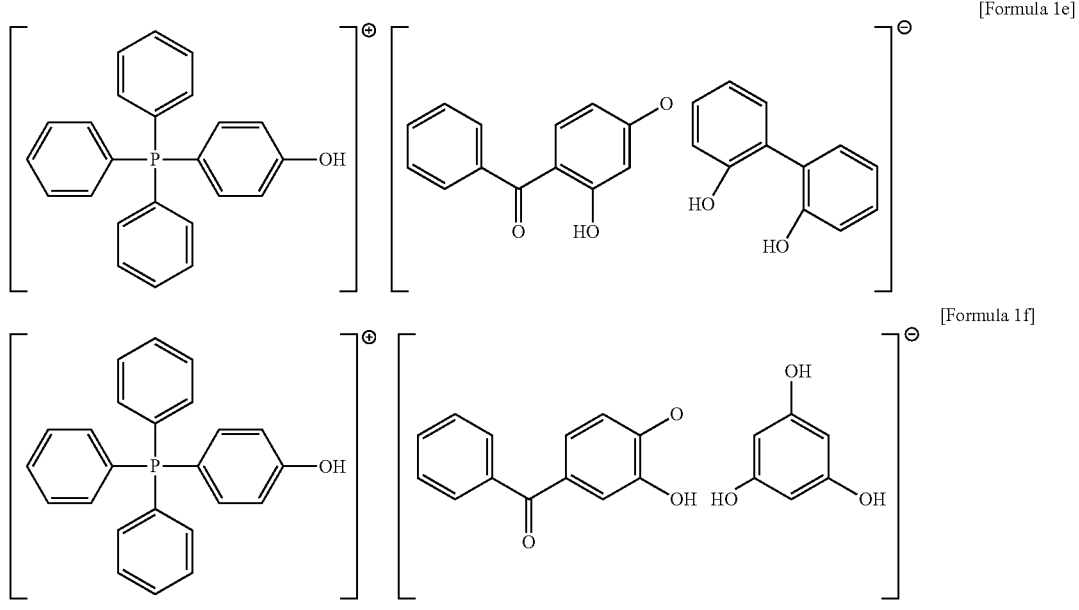

[Formula 1e]

[Formula 1f]

The phosphonium compound may be added to a composition including at least one of an epoxy resin, a curing agent, and inorganic fillers so as to be used as a latent curing catalyst.

The phosphonium compound according to the present invention may provide an epoxy resin composition capable of accelerating curing of an epoxy resin and a curing agent and capable of securing low temperature curability and high storage stability while minimizing viscosity change in a mixture including the compound together with an epoxy resin, a curing agent and the like even within desired ranges of time and temperature. Storage stability refers to an activity which catalyzes curing only at a desired curing temperature without any curing activity at temperature deviating from a desired curing temperature range. As a result, it is possible to store the epoxy resin composition for a long time without causing viscosity change. Generally, proceeding of curing reaction may cause increase in viscosity and deterioration in flowability when the epoxy resin composition is liquid and may exhibit viscosity when the epoxy resin composition is solid.

The phosphonium compound according to the present invention forms a mono valent anion through generation of clusters between different compounds having phenolic —OH groups. In the compound, the positions of cations and anions are appropriately arranged, thereby allowing ionic bonds between two molecules to be relatively strong. Since the clusters are formed by relatively weak hydrogen bonds, application of sufficient heat energy would rapidly break hydrogen bonds to disrupt anion clusters, thereby dissociating the cations and the anions, which would lead to fast curing reaction. Accordingly, the phosphonium compound may exhibit relatively long flowability while maintaining identical curing strength after being cured for identical curing time.

Epoxy Resin Composition

Next, an epoxy resin composition according to the present invention will be described.

The epoxy resin composition according to the present invention may include at least one of an epoxy resin, a curing agent, inorganic fillers, and a curing catalyst. In the following, each component of the epoxy resin composition of the present invention will be described in more detail.

(1) Epoxy Resin

The epoxy resin may have two or more epoxy groups per molecule. Example of epoxy resins include bisphenol A type epoxy resins, bisphenol F type epoxy resins, phenol novolac type epoxy resins, tert-butyl catechol type epoxy resins, naphthalene type epoxy resins, glycidyl amine type epoxy resins, cresol novolac type epoxy resins, biphenyl type epoxy resins, linear aliphatic epoxy resins, cycloaliphatic epoxy resins, heterocyclic epoxy resins, spiro ring-containing epoxy resins, cyclohexane dimethanol type epoxy resins, trimethylol type epoxy resins, and halogenated epoxy resins, without being limited thereto. These epoxy resins may be used alone or in combination thereof. For example, the epoxy resins may have two or more epoxy groups and one or more hydroxyl groups per molecule. The epoxy resins may include at least one of solid phase epoxy resins and liquid phase epoxy resins. The solid phase epoxy resin is preferably used.

In one embodiment, the epoxy resin may be a biphenyl type epoxy resin represented by Formula 2, a phenol aralkyl type epoxy resin represented by Formula 3 or a combination thereof:

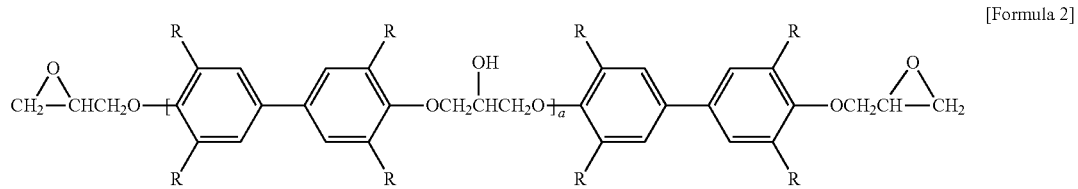

[Formula 2]

wherein Formula 2, R is a $C_1$ to $C_4$ alkyl group and a on average is 0 to 7.

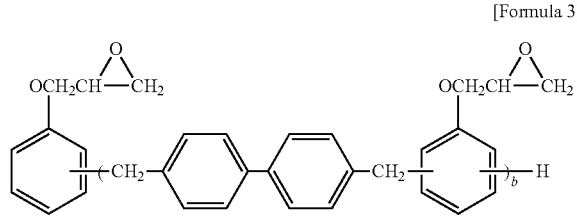

[Formula 3]

wherein Formula 3, b is 1 to 7 on average.

The composition may include the epoxy resin in an amount of about 2 wt % to about 17 wt %, for example, about 3 wt % to about 15 wt %, for example, about 3 wt % to about 12 wt % in terms of solid content. Within this range, the composition may secure curability.

(2) Curing Agent

The curing agent may include phenolaralkyl type phenol resins, phenol novolac type phenol resins, xyloc type phenol resins, cresol novolac type phenol resins, naphthol type phenol resins, terpene type phenol resins, multifunctional phenol resins, dicyclopentadiene-based phenol resins, novolac type phenol resins synthesized from bisphenol A and resol, polyhydric phenol compounds including tris(hydroxyphenyl)methane and dihydroxybiphenyl, acid anhydrides including maleic anhydride and phthalic anhydride, and aromatic amines including meta-phenylenediamine, diaminodiphenylmethane, diaminodiphenylsulfone, and the like. Preferably, the curing agent may be a phenol resin having one or more hydroxyl groups.

In one embodiment, the curing agent may be a xyloc type phenol resin represented by Formula 4, or a phenol aralkyl type phenol resin represented by Formula 5.

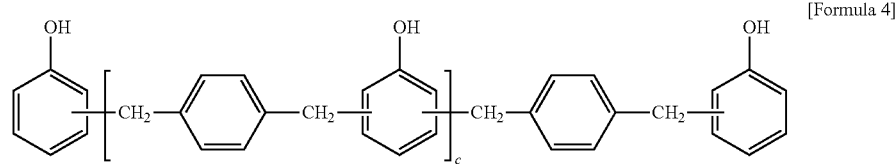

[Formula 4]

wherein Formula 4, c is 0 to 7 on average.

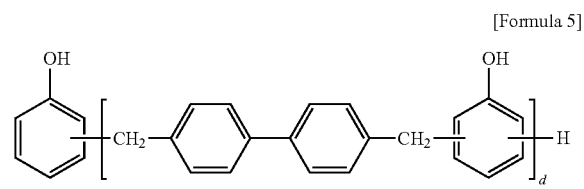

[Formula 5]

wherein Formula 5, d is 1 to 7 on average.

The epoxy resin composition may include the curing agent in an amount of about 0.5 wt % to about 13 wt %, for example, about 1 wt % to about 10 wt %, for example, about 2 wt % to about 8 wt % in terms of solid content. Within this range, the composition may secure curability.

(3) Inorganic Filler

The inorganic fillers are used to improve mechanical properties of the epoxy resin composition while reducing stress in the epoxy resin composition. Examples of the inorganic fillers include at least one of fused silica, crystalline silica, calcium carbonate, magnesium carbonate, alumina, magnesia, clay, talc, calcium silicate, titanium oxide, antimony oxide, and glass fibers.

Fused silica having a low coefficient of linear expansion is preferred in terms of stress reduction. The fused silica refers to amorphous silica having a specific gravity of 2.3 or less. The fused silica may be prepared by melting crystalline silica or may include amorphous silica products synthesized from various raw materials. The shape and particle diameter of the fused silica are not particularly limited. The inorganic fillers may include 40 wt % to 100 wt % of a fused silica mixture based on the total weight of the inorganic fillers, wherein the fused silica mixture includes about 50 wt % to about 99 wt % of spherical fused silica having an average particle diameter of about 5 μm to about 30 μm and about 1 wt % to about 50 wt % of spherical fused silica having an average particle diameter of about 0.001 μm to about 1 μm. The inorganic fillers may also be adjusted to a maximum particle diameter of 45 μm, 55 μm or 75 μm, depending upon application of the epoxy resin composition. The spherical fused silica may include conductive carbon as a foreign substance on the surface of silica. It is essential for the spherical fused silica to incorporate a smaller amount of polar foreign substances.

The inorganic fillers may be present in an appropriate amount depending upon desired physical properties of the epoxy resin composition, for example, moldability, low-stress properties, and high-temperature strength. Specifically, the inorganic fillers may be present in an amount of about 60 wt % to about 95 wt %, preferably about 75% to about 92 wt %, based on the total weight of the epoxy resin composition. Within this range, the epoxy resin composition may secure good flame resistance, flowability and reliability.

(4) Curing Catalyst

The epoxy resin composition may include a curing catalyst including the phosphonium compound represented by Formula 1. The phosphonium compound may be present in an amount of about 0.01 wt % to about 5 wt %, for example, about 0.02 wt % to about 1.5 wt %, for example, about 0.05 wt % to about 1.5 wt %, in the epoxy resin composition. Within this range, the epoxy resin composition may secure flowability without delaying time for curing reaction.

The epoxy resin composition may further include a non-phosphonium curing catalyst which does not contain phosphonium. Examples of non-phosphonium curing catalysts may include tertiary amines, organometallic compounds, organophosphorus compounds, imidazole, boron compounds, and the like. Examples of tertiary amines may include benzyldimethylamine, triethanolamine, triethylenediamine, diethylaminoethanol, tri(dimethylaminomethyl)

phenol, 2,2-(dimethylaminomethyl)phenol, 2,4,6-tris(diaminomethyl)phenol, tri-2-ethyl hexanoate, and the like. Examples of organometallic compounds include chromium acetylacetonate, zinc acetylacetonate, nickel acetylacetonate, and the like. Examples of organophosphorus compounds may include tris-4-methoxyphosphine, triphenylphosphine, triphenylphosphinetriphenylboran, triphenylphosphine-1,4-benzoquinone adducts, and the like. Examples of imidazoles may include 2-methylimidazole, 2-phenylimidazole, 2-aminoimidazole, 2-methyl-1-vinylimidazole, 2-ethyl-4-methylimidazole, 2-heptadecyl imidazole, and the like. Examples of boron compounds may include triphenylphosphine tetraphenyl borate, tetraphenyl borate, trifluoroborane-n-hexylamine, trifluoroborane monoethylamine, tetrafluoroborane triethylamine, tetrafluoroboraneamine, and the like. In addition, it is possible to use 1,5-diazabicyclo[4.3.0]non-5-ene (DBN), 1,8-diazabicyclo[5.4.0]undec-7-ene (DBU), phenol novolac resin salt, and the like. Particularly, the organophosphorus compounds, the boron compounds, and the amines or imidazole curing accelerators may be used alone or in combination. Adducts obtained by pre-reacting an epoxy resin or a curing agent may be used as the curing catalyst.

The phosphonium compound according to the present invention is present in an amount of about 10 wt % to about 100 wt %, for example, about 60 wt % to about 100 wt %, based on total weight of the curing catalyst. Within this range, the epoxy resin composition may secure flowability without delaying time for curing reaction.

The curing catalyst may be present in an amount of about 0.01 wt % to about 5 wt %, for example, about 0.02 wt % to about 1.5 wt %, for example, about 0.05 wt % to about 1.5 wt %, in the epoxy resin composition. Within this range, the epoxy resin composition may secure flowability without delaying time for curing reaction.

The composition according to the present invention may further include a typical additive. In one embodiment, the additive may include at least one of a coupling agent, a release agent, a stress reliever, a crosslinking enhancer, a leveling agent, and a coloring agent.

The coupling agent may include at least one selected from among epoxysilane, aminosilane, mercaptosilane, alkylsilane, and alkoxysilane, without being limited thereto. The coupling agent may be present in an amount of about 0.1 wt % to about 1 wt % in the epoxy resin composition.

The release agent may include at least one selected from among paraffin wax, ester wax, higher fatty acids, metal salts of higher fatty acids, natural fatty acids, and natural fatty acid metal salts. The mold release agent may be present in an amount of about 0.1 wt % to about 1 wt % in the epoxy resin composition.

The stress reliever may include at least one selected from among modified silicone oil, silicone elastomers, silicone powder, and silicone resin, without being limited thereto. The stress reliever may be optionally present in an amount of about 6.5 wt % or less, for example, about 1 wt % or less, for example, about 0.1 wt % to about 1 wt % in the epoxy resin composition. As the modified silicone oil, any silicone polymers having good heat resistance may be used. The modified silicone oil may include about 0.05 wt % to about 1.5 wt % of a silicone oil mixture based on the total weight of the epoxy resin composition, wherein the mixture includes at least one selected from the group consisting of silicone oil having an epoxy functional group, silicone oil having an amine functional group, silicone oil having a carboxyl functional group, and a combination thereof. However, if the amount of the silicone oil is greater than 1.5 wt %, surface contamination occurs easily and lengthy resin bleed may be encountered. If the amount of the silicone oil is less than 0.05 wt %, there may be a problem in that sufficiently low modulus of elasticity cannot be obtained. In addition, the silicone powder having an average particle diameter of 15 μm is particularly preferred in that the powder does not deteriorate moldability. The silicone powder may be optionally present in an amount of 5 wt % or less, for example, 0.1 wt % to 5 wt %, based on the total weight of the epoxy resin composition.

The additive may be present in an amount of 0.1 wt % to 10 wt %, for example, 0.1 wt % to 3 wt %, in the epoxy resin composition.

The epoxy resin composition is curable at low temperature. For example, a curing initiation temperature may range from 90° C. to 120° C. Within this range, the epoxy resin composition may be cured at low temperature, thereby securing curing at low temperature.

The epoxy resin composition may have a flow length of 50 inches to 95 inches, preferably 65 inches to 85 inches measured using a transfer molding press at 175° C. and 70 kgf/cm² in accordance with EMMI-1-66. Within this range, the epoxy resin composition may be used in a broad range of applications in encapsulation of semiconductor devices, adhesive films, insulating resin sheets such as prepregs and the like, circuit boards, solder resists, underfills, die bonding materials, component replenishing resins, and the like.

The epoxy resin composition may have a curing shrinkage rate of 0.40% or less, for example 0.01% to 0.39%, as calculated according to Equation 1. Within this range, the epoxy resin composition may be used in a broad range of applications requiring such an epoxy resin composition in encapsulation of semiconductor devices, adhesive films, insulating resin sheets such as prepregs and the like, circuit boards, solder resists, underfills, die bonding materials, component replenishing resins, and the like.

$$\text{Curing shrinkage} = |C-D|/C \times 100 \quad \text{[Equation 1]}$$

wherein Equation 1, C is the length of a specimen obtained by transfer molding of an epoxy resin composition at 175° C. under a load of 70 kgf/cm², and D is the length of the specimen after post-curing the specimen at 170° C. to 180° C. for 4 hours and cooling.

The epoxy resin composition may have storage stability of about 80% or more, preferably about 90% or more, as calculated according to Equation 2:

$$\text{Storage stability} = (F1-F0)/F0 \times 100 \quad \text{[Equation 2]}$$

wherein Equation 2, F1 is the flow length (inches) of the epoxy resin composition measured after storing the composition at 25° C./50% RH for 72 hours using a transfer molding press at 175° C. and 70 kgf/cm² in accordance with EMMI-1-66, and F0 is the initial flow length (inches) of the epoxy resin composition.

In the epoxy resin composition, the epoxy resin may be used alone or in the form of adducts, such as a melt master batch, obtained by pre-reacting the epoxy resin with an additive, such as a curing agent, a curing catalyst, a release agent, a coupling agent, and a stress reliever. Although there is no particular restriction as to the method of preparing the epoxy resin composition according to the present invention, the epoxy resin composition may be prepared by uniformly mixing all components of the resin composition using a suitable mixer, such as a Henschel mixer or a Redige mixer, followed by melt-kneading in a roll mill or a kneader at 90° C. to 120° C., cooling, and pulverizing.

The epoxy resin composition according to the present invention can be used in a broad range of applications requiring such an epoxy resin composition in encapsulation of semiconductor devices, adhesive films, insulating resin sheets such as prepregs and the like, circuit substrates, solder resists, underfills, die bonding materials, and component replenishing resins, without being limited thereto.

Encapsulation of Semiconductor Device

Next, a semiconductor device according to the present invention will be described.

The semiconductor device according to the present invention may be encapsulated with the epoxy resin composition.

FIG. 1 is a cross sectional view of a semiconductor device according to one embodiment of the present invention. Referring to FIG. 1, a semiconductor device 100 according to one embodiment includes a wiring board 10, bumps 30 formed on the wiring board 10, and a semiconductor chip 20 formed on the bumps 30, wherein a gap between the wiring board 10 and the semiconductor chip 20 is encapsulated with an epoxy resin composition 40, and the epoxy resin composition may be an epoxy resin composition according to embodiments of the present invention.

FIG. 2 is a cross sectional view of a semiconductor device according to another embodiment of the present invention. Referring to FIG. 2, a semiconductor device 200 according to another embodiment includes a wiring board 10, bumps 30 formed on the wiring board 10, and a semiconductor chip 20 formed on the bumps 30, wherein a gap between the wiring board 10 and the semiconductor chip 20 and the entirety of a top surface of the semiconductor chip 20 are encapsulated with an epoxy resin composition 40, and the epoxy resin composition may be an epoxy resin composition according to embodiments of the present invention.

FIG. 3 is a cross sectional view of a semiconductor device according to a further embodiment of the present invention.

Referring to FIG. 3, a semiconductor device 300 according to a further embodiment includes a wiring board 10, bumps 30 formed on the wiring board 10, and a semiconductor chip 20 formed on the bumps 30, wherein a gap between the wiring board 10 and the semiconductor chip 20 and the entirety of a side surface of the semiconductor chip 20 except for the top surface are encapsulated with an epoxy resin composition 40, and the epoxy resin composition may be an epoxy resin composition according to embodiments of the present invention.

In FIGS. 1 to 3, the size of each wiring board, bump and semiconductor chip, and the numbers of the bumps are optional and may be modified.

The semiconductor device may be encapsulated most commonly with the epoxy resin composition by low-pressure transfer molding. However, the semiconductor device may also be molded by injection molding, casting, and the like. The semiconductor device that can be fabricated by such a molding process may include a copper lead frame, an iron lead frame, an iron lead frame pre-plated with at least one metal selected from among nickel, copper and palladium, or an organic laminate frame.

[Mode for Invention]

Next, the present invention will be described in more detail with reference to some examples. It should be understood that these examples are provided for illustration only and are not to be construed in any way as limiting the present invention.

EXAMPLES

Preparative Example 1

Preparation of Phosphonium Compound Represented by Formula 1a 13.5 g of 3,4-Dihydroxybenzonitrile and 17.0 g of 2-phenylphenol were added to 50 g of MeOH, followed by adding 21.6 g of 25% sodium methoxide solution, which in turn was completely dissolved while reacting at room temperature for 30 minutes. To the solution, a solution of 41.9 g of tetraphenylphosphonium bromide previously dissolved in 50 g of methanol was slowly added, and the mixture was allowed to further react for 1 hour, followed by introducing 300 g of distilled water. The resulting white solid was filtered to obtain 54 g of a compound. The compound was identified based on NMR data as a compound represented by Formula 1a.

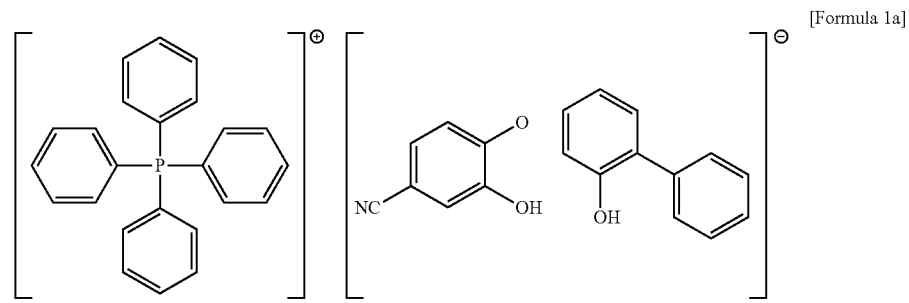

[Formula 1a]

1H NMR δ 8.00-7.94 (4H, dt), 7.85-7.70 (16H, m), 7.44-7.38 (6H, m), 6.88-6.83 (6H, m)

Preparative Example 2

Preparation of Phosphonium Compound Represented by Formula 1b 21.4 g of 3,4-Dihydorxybenzophenone and 12.4 g of 4-methylcatechol were added to 50 g of MeOH, followed by adding 21.6 g of 25% sodium methoxide solution, which in turn was completely dissolved while reacting at room temperature for 30 minutes. To the solution, a solution of 41.9 g of tetraphenylphosphonium bromide previously dissolved in 50 g of methanol was slowly added and the mixture was allowed to further react for 1 hour, followed by introducing 300 g of distilled water. The resulting brown solid was filtered to obtain 60 g of a compound. The compound was identified based on NMR data as a compound represented by Formula 1b.

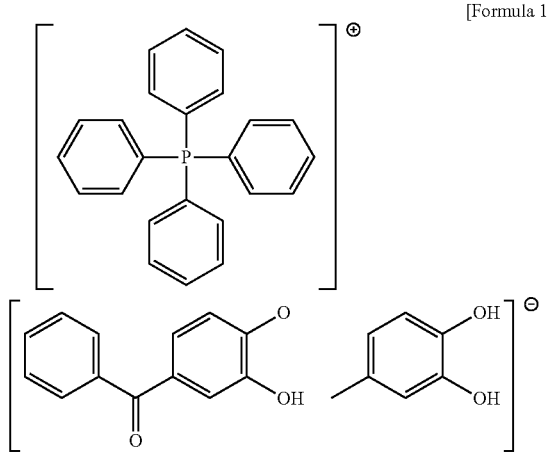

[Formula 1b]

1H NMR δ 8.00-7.94 (4H, dt), 7.85-7.70 (16H, m), 7.60 (2H, d), 7.43-7.38 (3H, m), 7.09 (1H, d), 6.97 (1H, s), 6.75-6.71 (3H, m), 6.51 (1H, d), 2.21 (3H, s)

Preparative Example 3

Preparation of Phosphonium Compound Represented by Formula 1c 21.4 g of 3,4-Dihydorxybenzophenone and 35.0 g of 9,9-bis(4-hydroxyphenyl)fluorene were added to 50 g of MeOH, followed by adding 21.6 g of 25% sodium methoxide solution, which in turn was completely dissolved while reacting at room temperature for 30 minutes. To the solution, a solution of 41.9 g of tetraphenylphosphonium bromide previously dissolved in 50 g of methanol was slowly added, and the mixture was allowed to further react for 1 hour, followed by introducing 300 g of distilled water. The resulting white solid was filtered to obtain 66 g of a compound. The compound was identified based on NMR data as a compound represented by Formula 1c.

[Formula 1c]

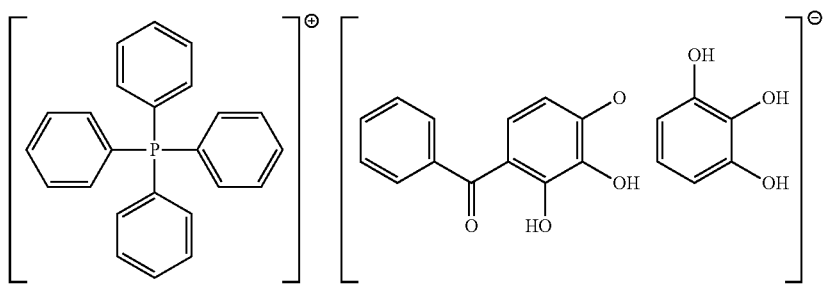

1H NMR δ 8.00-7.94 (4H, dt), 7.85-7.70 (18H, m), 7.60 (2H, d), 7.47 (2H, d), 7.30-7.24 (8H, m), 6.88 (4H, d), 6.61 (4H, d), 6.34 (1H, d), 6.21 (1H, s)

Preparative Example 4

Preparation of Phosphonium Compound Represented by Formula 1d 23.0 g of 2,3,4-trihydorxybenzophenone and 12.4 g of pyrogallol were added to 50 g of MeOH, followed by adding 21.6 g of 25% sodium methoxide solution, which in turn was completely dissolved while reacting at room temperature for 30 minutes. To the solution, a solution of 41.9 g of tetraphenylphosphonium bromide previously dissolved in 50 g of methanol was slowly added, and the mixture was allowed to further react for 1 hour, followed by introducing 300 g of distilled water. The resulting brown solid was filtered to obtain 61 g of a compound. The compound was identified based on NMR data as a compound represented by Formula 1d.

[Formula 1d]

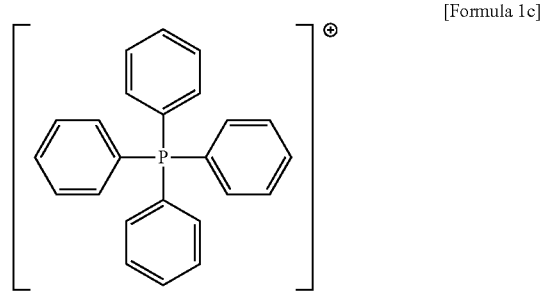

1H NMR δ 8.00-7.94 (4H, dt), 7.85-7.70 (16H, m), 7.60 (2H, d), 7.32-7.27 (3H, m), 6.96 (1H, d), 6.55-6.50 (2H, m), 6.06 (2H, d)

Preparative Example 5

Preparation of Phosphonium Compound Represented by Formula 1e

To a 1 L round bottom flask, 100 g of triphenylphosphine, 60 g of 4-Bromophenol, and 3.7 g of NiBr$_2$ were introduced, followed by adding 130 g of ethylene glycol, and then reacted at 180° C. for 6 hours, thereby obtaining a phosphonium bromide (salt) represented by Formula 1e' having a substituted phenol.

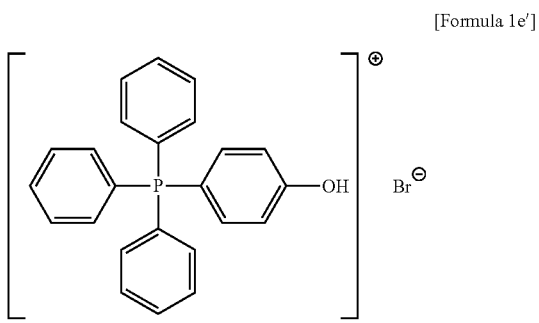

21.4 g of 2,4-Dihydroxybenzophenone and 18.4 g of 2,2-biphenol were added to 50 g of MeOH, followed by adding 21.6 g of 25% sodium methoxide solution, which in turn was completely dissolved while reacting at room temperature for 30 minutes. To the solution, a solution of 43.5 g of the phosphonium bromide (salt) represented by Formula 1e' previously dissolved in 50 g of methanol was slowly added, and the mixture was allowed to further react for 1 hour, followed by introducing 300 g of distilled water. The resulting white solid was filtered to obtain 68 g of a compound. The compound was identified based on NMR data as a compound represented by Formula 1e.

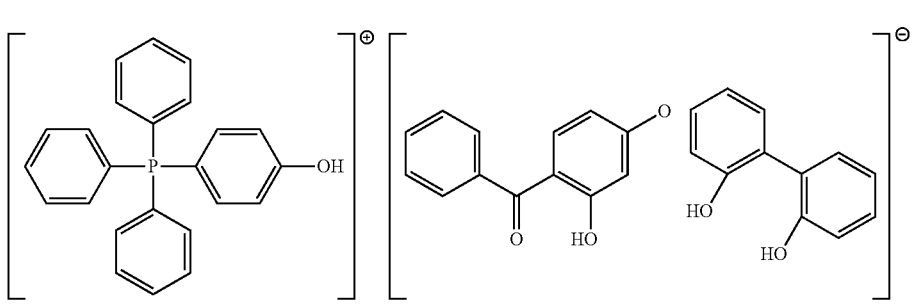

1H NMR δ 7.87 (3H, t), 7.77-7.73 (6H, m), 7.69-7.65 (6H,m), 7.60 (2H, d), 7.39 (1H, dd), 7.32 (2H, d), 7.28-7.24 (3H, m), 7.08-7.02 (4H, m), 6.88 (2H, dd), 6.79 (2H, d), 6.55 (2H, dd), 6.34 (1H, d), 6.21 (1H, s)

Preparative Example 6

Preparation of Phosphonium Compound Represented by Formula 1f 21.4 g of 3,4-dihydroxybenzophenone and 12.4 g of phloroglucinol were added to 50 g of MeOH, followed by adding 21.6 g of 25% sodium methoxide solution, which in turn was completely dissolved while reacting at room temperature for 30 minutes. To the solution, a solution of 43.5 g of the phosphonium bromide (salt) represented by Formula 1e' previously dissolved in 50 g of methanol was slowly added, and the mixture was allowed to further react for 1 hour, followed by introducing 300 g of distilled water. The resulting white solid was filtered to obtain 61 g of a compound. The compound was identified based on NMR data as a compound represented by Formula 1 f.

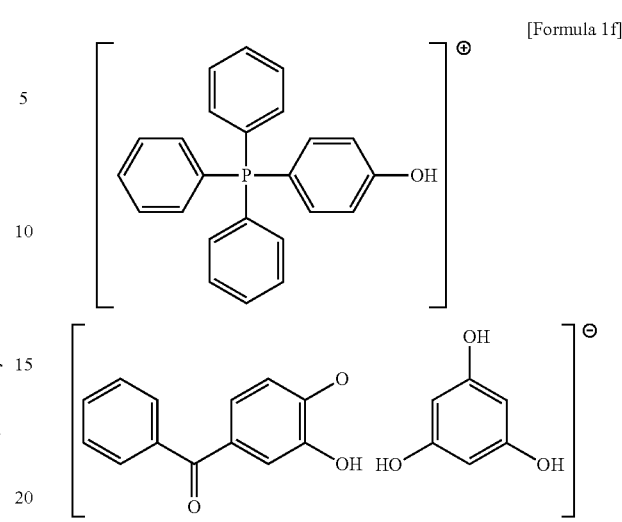

1H NMR δ 7.87 (3H, t), 7.77-7.73 (6H, m), 7.69-7.65 (6H,m), 7.60 (2H, d), 7.42-7.37 (3H, m), 7.09 (1H, d), 6.97 (1H, s), 6.88 (2H, dd), 6.55 (2H, dd), 6.51 (1H, d), 5.83 (3H, s)

Details of the components used in Examples and Comparative Examples are as follows.

(A) Epoxy resin

NC-3000 (manufactured by Nippon Kayaku) was used as a biphenyl type epoxy resin.

(B) Curing agent

HE100C-10 (manufactured by Air Water) was used as a xyloc type phenol resin.

(C) Curing catalyst

Phosphonium compounds prepared in Preparative Examples 1 to 6 were used as (C1) to (C6).

(C7) Triphenyl phosphine (C8) An adduct of triphenyl phosphine and 1,4-benzoquinone (D) Inorganic filler: A mixture of spherical fused silica having an average particle diameter of 18 μm and spherical fused silica having an average particle diameter of 0.5 μm (in a weight ratio of 9:1) was used.

(E) Coupling agent

A mixture of (e1) mercaptopropyl trimethoxy silane, KBM-803 (manufactured by Shinetsu Co., Ltd.) and (e2) methyl trimethoxy silane, SZ-6070 (manufactured by Dow Corning Chemical Co., Ltd.) was used.

(F) Additive (f1) Carnauba wax as a mold release agent, and (f2) Carbon black, MA-600 (manufactured by Matsushita Chemical Co., Ltd.) as a coloring agent, were used.

Examples and Comparative Examples

The components were weighed as listed in Table 1 to 3 (unit: parts by weight) and uniformly mixed using a Henschel mixer to prepare first powder compositions. Then, each of the compositions was melt-kneaded by a continuous kneader at 95° C., cooled, and pulverized to prepare an epoxy resin composition for encapsulation of a semiconductor device.

TABLE 1

| Component | | Example | | | | | | Comparative Example | |
|---|---|---|---|---|---|---|---|---|---|
| | | 1 | 2 | 3 | 4 | 5 | 6 | 1 | 2 |
| (A) | | 8.6 | 8.6 | 8.6 | 8.6 | 8.6 | 8.6 | 8.6 | 8.6 |
| (B) | | 5.0 | 5.0 | 5.0 | 5.0 | 5.0 | 5.0 | 5.0 | 5.0 |
| (C) | C1 | 0.4 | — | — | — | — | — | — | — |
| | C2 | — | 0.4 | — | — | — | — | — | — |
| | C3 | — | — | 0.4 | — | — | — | — | — |
| | C4 | — | — | — | 0.4 | — | — | — | — |
| | C5 | — | — | — | — | 0.4 | — | — | — |
| | C6 | — | — | — | — | — | 0.4 | — | — |
| | C7 | — | — | — | — | — | — | 0.4 | — |
| | C8 | — | — | — | — | — | — | — | 0.4 |
| (D) | | 85 | 85 | 85 | 85 | 85 | 85 | 85 | 85 |
| (E) | (e1) | 0.2 | 0.2 | 0.2 | 0.2 | 0.2 | 0.2 | 0.2 | 0.2 |
| | (e2) | 0.2 | 0.2 | 0.2 | 0.2 | 0.2 | 0.2 | 0.2 | 0.2 |
| (F) | (f1) | 0.3 | 0.3 | 0.3 | 0.3 | 0.3 | 0.3 | 0.3 | 0.3 |
| | (f2) | 0.3 | 0.3 | 0.3 | 0.3 | 0.3 | 0.3 | 0.3 | 0.3 |
| Total | | 100 | 100 | 100 | 100 | 100 | 100 | 100 | 100 |

The epoxy resin compositions prepared in Examples and Comparative Examples and packages in which the corresponding epoxy resin composition was employed were evaluated for their physical properties listed in Table 2 by way of the following measuring methods.

(1) Flowability (inches): The flow length of each of the epoxy resin compositions was measured using a transfer molding press in a testing mold at 175° C. and 70 kgf/cm$^2$ in accordance with EMMI-1-66. A higher measured value indicates better flowability.

(2) Curing shrinkage (%): Each of the epoxy resin compositions was molded using a transfer molding press in an ASTM mold for flexural strength specimen construction at 175° C. and 70 kgf/cm$^2$ to obtain a molded specimen (125×12.6×6.4 mm). The specimen was subjected to post-molding curing (PMC) in an oven at 170° C. to 180° C. for 4 h. After cooling, the length of the specimen was measured using calipers. Curing shrinkage of the epoxy resin composition was calculated according to Equation 1:

Curing shrinkage=|C−D|/C×100  <Equation 1> wherein Equation 1, C is the length of a specimen obtained by transfer molding of an epoxy resin composition at 175° C. under a load of 70 kgf/cm$^2$, and D is the length of the specimen after post-curing the specimen at 170° C. to 180° C. for 4 hours and cooling.

(3) Glass transition temperature (° C.) was measured using a thermomechanical analyzer (TMA) while heating at a rate of 10° C./min from 25° C. to 300° C.

(4) Moisture absorption (%): Each of the resin compositions prepared in Examples and Comparative Examples was molded at a mold temperature of 170° C. to 180° C., a clamp pressure of 70 kg/cm$^2$, a transfer pressure of 1,000 psi and a transfer speed of 0.5 cm/s to 1 cm/s for a curing time of 120 sec to obtain a cured specimen in the form of a disc having a diameter of 50 mm and a thickness of 1.0 mm. The specimen was subjected to post-molding curing (PMC) in an oven at 170° C. to 180° C. for 4 hours and allowed to stand at 85° C. and 85% RH for 168 hours. The weights of the specimen before and after moisture absorption were measured. The moisture absorption of the resin composition was calculated according to Equation 3:

Moisture absorption (%)=(Weight of the specimen after moisture absorption−Weight of the specimen before moisture absorption)÷(Weight of the specimen before moisture absorption)×100  <Equation 3>

(5) Adhesive strength (kgf): A copper metal device having a size adapted to a mold for adhesive strength measurement was prepared as a test piece. Each of the resin compositions prepared in Examples and Comparative Examples was molded on the test piece at a mold temperature of 170° C. to 180° C., a clamp pressure of 70 kgf/cm$^2$, a transfer pressure of 1,000 psi and a transfer speed of 0.5 cm/s to 1 cm/s for a curing time of 120 sec to obtain a cured specimen. The specimen was subjected to post-molding curing (PMC) in an oven at 170° C. to 180° C. for 4 hours. The area of the epoxy resin composition in contact with the specimen was 40 ±1 mm$^2$. The adhesive strength of the epoxy resin composition was measured using a universal testing machine (UTM). 12 specimens of each composition were produced. After the measurement procedure was repeated, the measured adhesive strength values were averaged.

(6) Degree of cure (Shore-D): Each of the epoxy resin compositions was cured using a multi plunger system (MPS) equipped with a mold at 175° C. for 50 sec, 60 sec, 70 sec, 80 sec, and 90 sec to construct exposed thin quad flat packages (eTQFPs), each including a copper metal device having a width of 24 mm, a length of 24 mm and a thickness of 1 mm. The hardness values of the cured products in the packages on the mold according to the curing periods of time were directly measured using a Shore D durometer. A higher hardness value indicates better degree of cure.

(7) Storage stability (%): The flow length of each of the epoxy resin compositions was measured in accordance with the method described in (1) while storing the compositions for one week in a thermo-hygrostat set to at 25° C./50% RH at an interval of 24 hours. Percent (%) of the flow length after the storage to the flow length immediately after preparation of the composition was calculated. A higher value indicates better storage stability.

TABLE 2

| | | Example | | | | | | Comparative Example | |
|---|---|---|---|---|---|---|---|---|---|
| | | 1 | 2 | 3 | 4 | 5 | 6 | 1 | 2 |
| | Flowability (inch) | 73 | 77 | 74 | 75 | 76 | 76 | 49 | 55 |
| Basic | Curing shrinkage (%) | 0.33 | 0.32 | 0.34 | 0.33 | 0.32 | 0.31 | 0.41 | 0.41 |
| physical | Glass transition temp. (° C.) | 124 | 124 | 122 | 120 | 124 | 125 | 121 | 124 |

TABLE 2-continued

|  |  |  | Example | | | | | | Comparative Example | |
| --- | --- | --- | --- | --- | --- | --- | --- | --- | --- | --- |
|  |  |  | 1 | 2 | 3 | 4 | 5 | 6 | 1 | 2 |
| properties | Moisture absorption (%) |  | 0.22 | 0.22 | 0.24 | 0.23 | 0.24 | 0.22 | 0.25 | 0.26 |
|  | Adhesive strength (kgf) |  | 75 | 75 | 76 | 74 | 75 | 74 | 74 | 76 |
| Evaluation of packages | Degree of cure (Shore-D) according to curing time | 40 sec | 65 | 67 | 65 | 68 | 68 | 64 | 51 | 66 |
|  |  | 50 sec | 72 | 71 | 72 | 72 | 71 | 72 | 56 | 68 |
|  |  | 60 sec | 73 | 74 | 73 | 74 | 73 | 73 | 58 | 69 |
|  |  | 70 sec | 74 | 74 | 75 | 76 | 76 | 75 | 62 | 72 |
|  |  | 80 sec | 74 | 76 | 75 | 76 | 76 | 76 | 63 | 74 |
|  | Storage stability | 24 hrs | 95% | 94% | 95% | 94% | 94% | 96% | 80% | 85% |
|  |  | 48 hrs | 93% | 92% | 93% | 93% | 92% | 94% | 70% | 75% |
|  |  | 72 hrs | 90% | 90% | 91% | 90% | 89% | 91% | 55% | 63% |

It could be seen that the epoxy resin compositions prepared in Examples 1 to 6 had higher flowability and higher degree of cure even in shorter curing periods of time in view of curability for each curing period of time than the epoxy resin compositions of Comparative Examples 1 and 2. For storage stability, it was apparent that the epoxy resin compositions of Examples 1 to 6 showed less change in flowability after 72 hours of storage.

On the contrary, the compositions prepared in Comparative Examples 1 and 2 not including the phosphonium compound of the present invention have low storage stability, high curing shrinkage, and low flowability. Therefore, it could be seen that the compositions of Comparative Examples 1 and 2 in a package could not ensure the effects of the present invention.

Although some embodiments have been described herein, it will be apparent to those skilled in the art that these embodiments are given by way of illustration only, and that various modifications, changes, alterations, and equivalent embodiments can be made without departing from the spirit and scope of the invention. The scope of the invention should be limited only by the accompanying claims and equivalents thereof.

The invention claimed is:

1. A phosphonium compound, wherein the phosphonium compound is any one of compounds represented by Formulae 1a to 1f:

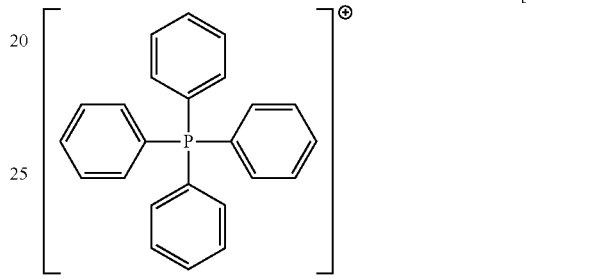

[Formula 1a]

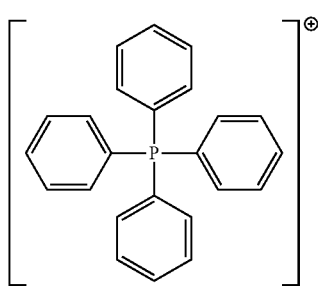

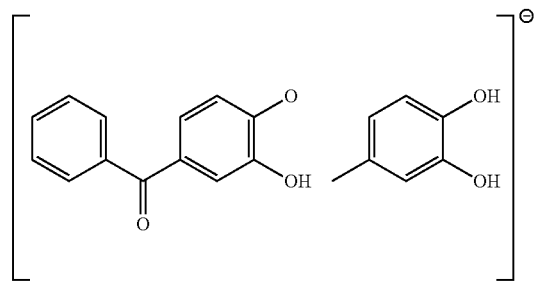

[Formula 1b]

[Formula 1c]

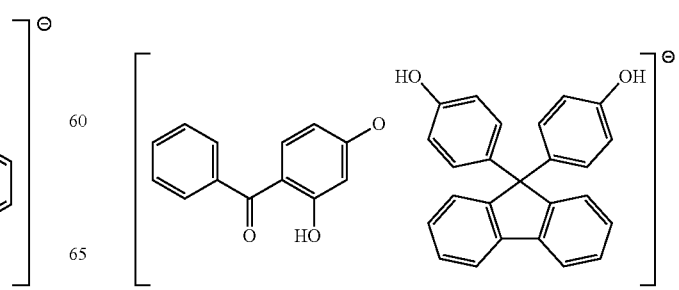

[Formula 1d]

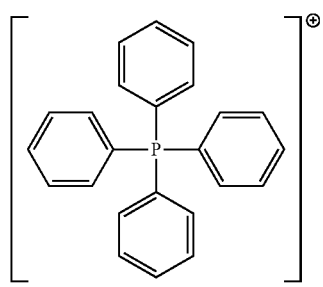

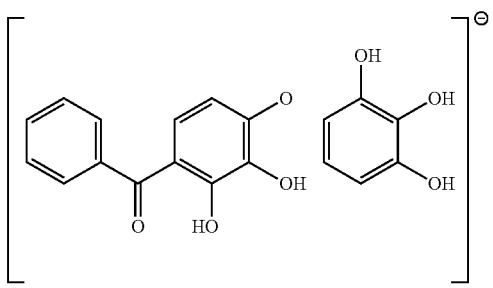

[Formula 1e]

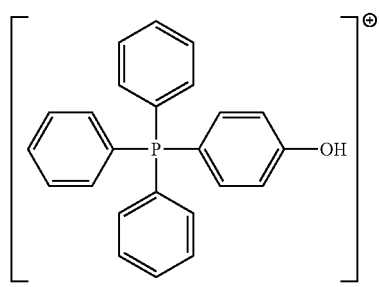

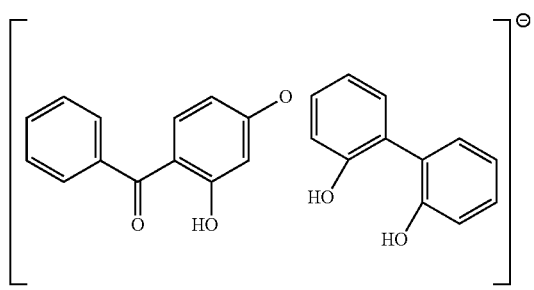

[Formula 1f]

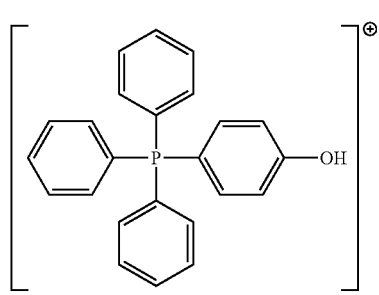

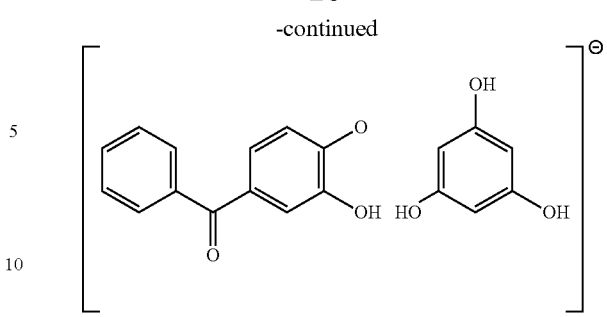

2. An epoxy resin composition, comprising:
an epoxy resin, a curing agent, an inorganic filler, and a curing catalyst, the curing catalyst including the phosphonium compound according to claim 1.

3. The epoxy resin composition according to claim 2, wherein the epoxy resin includes one or more of a bisphenol A type epoxy resin, a bisphenol F type epoxy resin, a phenol novolac type epoxy resin, a tert-butyl catechol type epoxy resin, a naphthalene type epoxy resin, a glycidyl amine type epoxy resin, a cresol novolac type epoxy resin, a biphenyl type epoxy resin, a linear aliphatic epoxy resin, a cycloaliphatic epoxy resin, a heterocyclic epoxy resin, a spiro ring-containing epoxy resin, a cyclohexane dimethanol type epoxy resin, a trimethylol type epoxy resin, or a halogenated epoxy resin.

4. The epoxy resin composition according to claim 2, wherein the curing agent includes a phenol resin.

5. The epoxy resin composition according to claim 2, wherein the curing agent includes one or more of a phenolaralkyl type phenol resin, a phenol novolac type phenol resin, a xyloc type phenol resin, a cresol novolac type phenol resin, a naphthol type phenol resin, a terpene type phenol resin, a multifunctional phenol resin, a dicyclopentadiene-based phenol resin, a novolac type phenol resin synthesized from bisphenol A and resol, a polyhydric phenol compound, an acid anhydride, or an aromatic amine.

6. The epoxy resin composition according to claim 2, wherein the curing catalyst is present in an amount of 0.01 wt % to 5 wt % in the epoxy resin composition.

7. The epoxy resin composition according to claim 2, wherein the phosphonium compound is present in an amount of 10 wt % to 100 wt % in the curing catalyst.

8. The epoxy resin composition according to claim 2, wherein the epoxy resin composition has a curing shrinkage of not more than 0.4%, as calculated according to Equation 1:

$$\text{Curing shrinkage}=|C-D|/C \times 100 \quad \text{<Equation 1>}$$

wherein C is the length of a specimen obtained by transfer molding of the epoxy resin composition at 175° C. and 70 kgf/cm², and D is the length of the specimen after post-curing the specimen at 170° C. to 180° C. for 4 hours and cooling.

9. The epoxy resin composition according to claim 2, wherein the epoxy resin composition has a storage stability of about 80% or more, as calculated according to Equation 2:

$$\text{Storage stability}=(F1-F0)/F0 \times 100 \quad \text{<Equation 2>}$$

wherein F1 is the flow length (inches) of the epoxy resin composition measured after storing the composition at 25° C./50% RH for 72 hours using a transfer molding press at 175° C. and 70 kgf/cm² in accordance with EMMI-1-66, and F0 is the initial flow length (inches) of the epoxy resin composition.

10. A semiconductor device encapsulated with the epoxy resin composition according to claim 2.

* * * * *